United States Patent
Hattori et al.

(10) Patent No.: US 10,406,086 B2
(45) Date of Patent: Sep. 10, 2019

(54) MOISTURIZER AND COSMETIC INCLUDING THE SAME

(71) Applicant: AJINOMOTO CO., INC., Tokyo (JP)

(72) Inventors: Gaku Hattori, Tokyo (JP); Hiroji Ishii, Kawasaki (JP); Fumie Honkawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 15/904,942

(22) Filed: Feb. 26, 2018

(65) Prior Publication Data

US 2018/0185256 A1 Jul. 5, 2018

Related U.S. Application Data

(63) Continuation of application No. PCT/JP2016/080880, filed on Oct. 18, 2016.

(30) Foreign Application Priority Data

Oct. 19, 2015 (JP) ................................. 2015-205605

(51) Int. Cl.
*A61K 8/44* (2006.01)
*A61Q 19/00* (2006.01)
*A61K 31/198* (2006.01)

(52) U.S. Cl.
CPC .............. *A61K 8/44* (2013.01); *A61K 31/198* (2013.01); *A61Q 19/00* (2013.01); *A61Q 19/007* (2013.01)

(58) Field of Classification Search
CPC ...................................................... A61K 8/44
USPC ....................................................... 514/563
See application file for complete search history.

(56) References Cited

U.S. PATENT DOCUMENTS

| 2006/0094610 A1 | 5/2006 | Yamato et al. |
| 2016/0082087 A1 | 3/2016 | Koizumi et al. |
| 2017/0020131 A1 | 1/2017 | Koshti et al. |

FOREIGN PATENT DOCUMENTS

| JP | 08337563 A | * 12/1996 |
| JP | 11-021582 | 1/1999 |
| JP | 11-080105 | 3/1999 |
| JP | 11-189788 | 7/1999 |
| JP | 2002-179553 | 6/2002 |
| JP | 2011-241188 | 12/2011 |
| JP | 2012-180293 | 9/2012 |
| JP | 2012-232920 | 11/2012 |
| JP | 2013-040123 | 2/2013 |
| WO | 2004/098558 | 11/2004 |
| WO | 2014/175001 | 10/2014 |
| WO | 2015/136546 | 9/2015 |

OTHER PUBLICATIONS

Englsih translation of JP 08337563 A (1996).*
The Englsh translation abstract for JP 08337563 A (1996).*
International Search Report in PCT/JP2016/080880 dated Dec. 20, 2016.
"Lipacidetm C8G Antiradicalaire, Antioxydant, Antiage, Anti Rides, Botox Like, Laser Like, Raffermissant, Amincissant, Estructurant, Cicatrisant, Stimulant, Decontractant, Hydratant, Emolient, Protecteur, Energisant, Oxygenant, Antimicrobien, Antibacterien, Antiongique, Antipelliculaire, Antitranspir", ip.com Journal, ip.com Inc., West Henrietta, NY, US. Jun. 26, 2006 (Jun. 26, 2006), XP013114692, ISSN: 1533-0001.
Extended Search Report dated May 14, 2019 issued in corresponding European patent application No. 16857442.4.

* cited by examiner

*Primary Examiner* — Kevin E Weddington
(74) *Attorney, Agent, or Firm* — Oblon, McClelland, Maier & Neustadt, L.L.P.

(57) ABSTRACT

Moisturizers including an acyl neutral amino acid having an acyl group with a carbon atom number of 2 to 18, and salts thereof, and cosmetics containing such a moisturizer promote the production of moisturizing-related proteins, such as filaggrin, involucrin, transglutaminase 1, keratin 10, and loricrin, and provide a moisturizing effect.

28 Claims, 5 Drawing Sheets

Amount of Filaggrin Gene Expression
(N = 2, mean ± SD)

FIG. 5

Amount of Filaggrin Gene Expression
(N = 2, mean ± SD)

FIG.6

MOISTURIZER AND COSMETIC INCLUDING THE SAME

CROSS REFERENCES TO RELATED APPLICATIONS

This application is a continuation of International Patent Application No. PCT/JP2016/080880, filed on Oct. 18, 2016, and claims priority to Japanese Patent Application No. 2015-205605, filed on Oct. 19, 2015, b of which are incorporated herein by reference in their entireties.

BACKGROUND OF THE INVENTION

Field of the Invention

The present invention relates to moisturizers and cosmetics including the same.

Discussion of the Background

Profilaggrin stored in the granular cell layer of skin tissue is decomposed into filaggrin through dephosphorylation during keratinization. Filaggrin migrates from the granular cell layer to a stratum corneum and binds to and aggregates with keratin fibers to form a keratin pattern. Filaggrin decomposes into small molecules such as urocanic acid and acts as a natural moisturizing factor related to water retention and ultraviolet absorption.

The marginal band is a part of the stratum corneum of the skin tissue and is a very strong and huge insoluble structure lining cell membranes of corneocytes. The main structural elements of the marginal band are proteins such as involucrin and loricrin, which are crosslinked by enzymes such as transglutaminase (TG) 1. Involucrin and loricrin are produced from prickle cells and granule cells, respectively. The marginal band includes a structure in which keratin such as keratin 10 and filaggrin aggregate.

It has been reported that expression of filaggrin, involucrin, transglutaminase 1, keratin 10, and loricrin is promoted by specific peptides such as glycylproline (see WO 2014/175001, which is incorporated herein by reference in its entirety) and piper longum extract (see Japanese Patent Application Laid-open No. 2012-232920, which is incorporated herein by reference in its entirety).

Either specific peptides such as glycylproline or the piper longum extract, however, has weak expression promoting action of moisturizing-related proteins such as filaggrin, and is insufficient to be utilized as the active component of a moisturizer.

Thus, there remains a need for improved moisturizers and cosmetics which contain such an improved moisturizer.

SUMMARY OF THE INVENTION

Accordingly, it is one object of the present invention to provide novel moisturizers.

It is another object of the present invention to provide novel cosmetics which contain such a moisturizer.

It is another object of the present invention to provide novel methods of moisturizing skin by applying such a moisturizer or cosmetic to skin.

These and other objects, which will become apparent during the following detailed description, have been achieved by the inventors' discovery that an acyl amino acid having a carbon atom number of 2 to 18 and a salt thereof can promote the production of the moisturizing-related proteins such as filaggrin, involucrin, transglutaminase 1, keratin 10, and loricrin and, as glycylproline, the acyl amino acid can reduce the production of an inflammatory cytokine that prevents moisturizing action.

Thus, the present invention provides the following:

(1) A moisturizer, comprising one or more compounds selected from the group consisting of an acyl neutral amino acid involving an acyl group having a carbon atom number of 2 to 18 and a salt thereof.

(2) The moisturizer according to (1), wherein the acyl neutral amino acid is one or more compounds selected from the group consisting of an acyl leucine, an acyl isoleucine, an acyl valine, an acyl glycine, and an acyl alanine.

(3) The moisturizer according to (1) or (2), wherein the carbon atom number of the acyl group is 2 to 12.

(4) The moisturizer according to any one of (1) to (3), wherein the carbon atom number of the acyl group is 2 to 10.

(5) The moisturizer according to any one of (1) to ([4), wherein the carbon atom number of the acyl group is 8.

(6) The moisturizer according to any one of (1) to (5), wherein the acyl neutral amino acid is one or more compounds selected from the group consisting of an acyl valine, an acyl glycine, and an acyl alanine.

(7) The moisturizer according to any one of (1) to (6), wherein the moisturizer promotes production of one or more moisturizing-related proteins selected from the group consisting of filaggrin, involucrin, transglutaminase 1, keratin 10, and loricrin.

(8) The moisturizer according to any one of (1) to (7), wherein the moisturizer reduces growth of an inflammatory cytokine.

(9) A cosmetic, comprising the moisturizer according to any one of (1) to (8).

(10) An external preparation for skin, the external preparation comprising the moisturizer according to any one of (1) to (8).

Advantageous Effects of Invention

The moisturizer of the present invention can exhibit sufficient moisturizing effect. The moisturizer of the present invention can promote the production of the moisturizing-related proteins. Consequently, the moisturizer of the present invention is useful for cosmetics.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The moisturizer of the present invention includes one or more compounds selected from the group consisting of an acyl neutral amino acid including an acyl group having a carbon atom number of 2 to 18 and a salt thereof.

The acyl neutral amino acid means a neutral amino acid substituted with an acyl group. The acyl group (alkanoyl group) is a group represented by a formula: —C(=O)—R (in the formula, R is an alkyl group) and may be either linear or branched. In the formula, R may contain one or more double bonds.

The lower limit of the carbon atom number in the acyl group is two or more and preferably three or more. The acyl neutral amino acid having such an acyl group can maintain the safety to skin. The upper limit of the carbon atom number in the acyl group is 18 or less, preferably 12 or less, and more preferably 11 or less. Consequently, the carbon atom number is 2 to 18, preferably 2 to 12, more preferably 3 to 11 or 2 to 10, and further preferably 8.

Examples of the acyl group may include an acetyl group, a butanoyl group, a pentanoyl group, a hexanoyl group, a heptanoyl group, an octanoyl group, a nonanoyl group, a decanoyl group, a dodecanoyl group, a tetradecanoyl group, a pentadecanoyl group, a 9-hexadecenoyl group, a hexadecanoyl group, an octadecanoyl group, a cis-9-octadecenoyl group, an 11-octadecenoyl group, a cis,cis-9,12-octadecenoyl group, a 9,12,15-octadecanetrieneoctadecadienoyl group, a 6,9,12-octadecatrienoyl group, and a 9,11,13-octadecatrienoyl group. Of these acyl groups, acyl groups having a carbon atom number of 2 to 12 such as the acetyl group, the butanoyl group, the pentanoyl group, the hexanoyl group, the heptanoyl group, the octanoyl group, the nonanoyl group, the decanoyl group, the dodecanoyl group, and the tetradecanoyl group are preferable. Acyl groups having a carbon atom number of 3 to 11 such as the pentanoyl group, the hexanoyl group, the heptanoyl group, the octanoyl group, the nonanoyl group, and the decanoyl group or acyl groups having a carbon atom number of 2 to 10 such as the acetyl group, the butanoyl group, the pentanoyl group, the hexanoyl group, the heptanoyl group, the octanoyl group, the nonanoyl group, and the decanoyl group are more preferable and acyl groups having a carbon atom number of 8 such as the octanoyl group is further preferable.

The number of acyl group(s) that the acyl neutral amino acid has may be one or may be a combination of two or more. The number of acyl group(s), however, is preferably one.

Examples of the neutral amino acids may include glycine, alanine, phenylalanine, tyrosine, tryptophan, proline, serine, threonine, cysteine, methionine, asparagine, glutamine, leucine, isoleucine, and valine. Leucine, isoleucine, valine, glycine, and alanine are preferable. The stereostructure of the neutral amino acid is not particularly limited. Any of L forms, D forms, and DL forms may be usable.

The salt of the acyl neutral amino acid may be the salt of the acyl neutral amino acid described above. The salt may be a pharmaceutically acceptable salt. Examples of such a salt may include alkali metal salts such as a potassium salt and a sodium salt; alkaline earth metal salts such as a calcium salt, a barium salt, and a magnesium salt; ammonium salts such as an ammonium salt and a tricyclohexyl ammonium salt; and alkanolamine salts such as a monoethanolamine salt, a diethanolamine salt, a triethanolamine salt, a monoisopropanolamine salt, a diisopropanolamine salt, and a triisopropanolamine salt.

A method for producing the acyl neutral amino acid and the salt thereof is not particularly limited. Examples of the method include a chemical synthesis method, a fermentation method, and a gene recombination method.

The acyl neutral amino acid and the salt thereof have production promotion action of one or more moisturizing-related proteins selected from the group consisting of filaggrin, involucrin, transglutaminase 1, keratin 10, and loricrin. This action can improve or maintain moisture retention of skin. Consequently, the acyl neutral amino acid and the salt thereof can also be used as an active component for production promoter for the moisturizing-related protein.

The moisturizer of the present invention may include one compound selected from the acyl neutral amino acid involving an acyl group having a carbon atom number of 2 to 18 and the salt thereof or may include two or more compounds. The moisturizer of the present invention may include a moisture retention component and/or a production promoter of the moisture retention component other than the acyl neutral amino acid involving an acyl group having a carbon atom number of 2 to 18 and an ester thereof, if needed.

The moisturizer of the present invention preferably includes the acyl neutral amino acid and the salt thereof that have no cytotoxicity. More preferably, the moisturizer of the present invention does not substantially include the acyl neutral amino acid and the salt thereof that has cytotoxicity. The phrase "do not have cytotoxicity" means that a cell survival rate when 10 to 500 µM of a sample is added to human epidermal keratinocytes (for example, calculated from light absorbance measured under conditions in Examples 25 to 30) is, for example, 75% or higher, 90% or higher, 95% or higher, or preferably 99% or higher. For example, the acyl neutral amino acid involving an acyl group having a carbon atom number of 12 (example of acyl neutral amino acid: valine) and the salt thereof may have cytotoxicity. The phrase "do not substantially include the acyl neutral amino acid and the salt thereof that have cytotoxicity (for example, the acyl neutral amino acid involving an acyl group having a carbon atom number of 12 and the salt thereof)" means that the content of the acyl neutral amino acid and the salt thereof that have cytotoxicity in the moisturizer is usually 30% by weight or lower, preferably 10% by weight or lower, more preferably 1% by weight or lower, and further preferably 0.5% by weight or lower in the total content of the acyl neutral amino acids and the salts thereof.

The moisturizer of the present invention may be included in a cosmetic or an external preparation for skin. The content of the moisturizer in the cosmetic and the external preparation for skin of the present invention can be adequately adjusted depending on the type of the cosmetic and the external preparation for skin and is not particularly limited. The suitable content in terms of the total amount of the acyl neutral amino acid and the salt thereof is preferably 0.001% by weight or higher and more preferably 0.05% by weight or higher when the cosmetic or the external preparation for skin is determined to be 100% by weight. The upper limit of the content is preferably 30% by weight or lower, more preferably 25% by weight or lower, and further preferably 5% by weight or lower.

The use form of the cosmetic of the present invention is not particularly limited. The cosmetic is usually applied to skin, nails, mucosa, and hair and is preferably used for skin. Therefore, examples of the dosage form of the cosmetic of the present invention include an aqueous solution, an emulsified product, a powder dispersion, and an emulsion (an oil-in-water type emulsion, a water-in-oil type emulsion, or the like). Specific examples include a liquid formulation, an oil formulation, a lotion, a gel, a sol, an emulsion, a suspension, a cream, an ointment, a patch, and a stick. Examples of what is called cosmetic include skin lotions such as a lotion and an beauty essence; emulsions such as an emollient emulsion, a milky lotion, a nourishing emulsion, and a cleansing emulsion; creams such as an emollient cream, a massage cream, a cleansing cream, and a make-up cream; a spray; cosmetics for make-up such as a facial pack, a foundation, a lip rouge, a lipstick, an eye shadow, a cheek color, a face powder, a color powder, and a manicure; cosmetic products for hair care such as a hair tonic, a shampoo, a rinse, and a hair lotion; and cosmetics for skin cleansing such as a facial wash, a makeup remover, a body shampoo, and a soap.

The external preparation for skin of the present invention can be used as a drug or a quasi-drug. Examples of the dosage form of the external preparation for skin of the present invention include a liquid, a lotion, an ointment, a cream, a plaster, a tape formulation, and a powder.

The cosmetic and the external preparation for skin of the present invention may include one or more base materials. The base material may be a base material used for common external preparations. Examples of the base material include an oily base material, a water-soluble base material, and a surfactant. Examples of the oily base material include vegetable oils and fats such as a cottonseed oil, a sesame oil, an olive oil, and a cocoa butter; waxes such as carnauba wax and beeswax; higher hydrocarbons such as a vaseline, a liquid paraffin, a solid paraffin, squalane, an olefin oligomer, and a plastibase; fatty acids such as stearic acid and palmitic acid and esters thereof; higher alcohols such as cetanol; silicones such as methylpolysiloxane, methylphenylpolysiloxane, a silicon fluid, a silicone rubber, and a silicone oil; base waxes such as a white kerosene, and natural macromolecules. Examples of the water-soluble base material include polyvinyl alcohol, carboxyvinyl polymers, cellulose derivatives (methyl cellulose, hydroxyethyl cellulose, hydroxypropyl cellulose, cationized cellulose, and the like), esters (isopropyl myristate, isopropyl palmitate, stearyl stearate, octyldodecyl myristate, octyldodecyl oleate, 2-ethylhexanoic acid triglyceride, and the like), polyols (ethylene glycol, polyethylene glycol, a polypropylene glycol copolymer, propylene glycol, dipropylene glycol, 1,3-butylene glycol, glycerol, and the like), and alcohols (ethanol and the like).

The cosmetic and the external preparation for skin of the present invention may include commonly used additive components, if needed. Examples of the additive components include emulsifiers, surfactants, viscosity modifiers, stabilizers, pH adjusters, preservatives, absorption promoters, pearl ingredients, anti-inflammatory agents, ultraviolet absorbers, ultraviolet scattering agents, other functional components (physiologically active components), flavoring agents, and coloring matter.

Examples of the emulsifiers include glyceryl monostearate, sorbitan monopalmitate, polyoxyethylene cetyl ethers, polyoxyethylene sorbitan monolaurates, and diglycerol monostearate ester.

Examples of the surfactants include anionic surfactants such as polyoxyethylene sorbitan oleates, higher fatty acid soaps, alkyl sulfates, polyoxyethylene alkyl ether sulfates, alkyl ether phosphates, N-acyl amino acid salts, and acyl N-methyl taurine salts; cationic surfactants such as alkyltrimethylammonium chlorides and dialkyldimethylammonium chlorides; amphoteric surfactants such as alkyldimethylaminoacetic acid betaines, alkylamidodimethylaminoacetic acid betaines, and 2-alkyl-N-carboxy-N-hydroxyimidazolinium betaines; and nonionic surfactants such as polyoxyethylene surfactants, polyhydric alcohol ester surfactants, and ethylene oxide-propylene oxide block copolymers.

Examples of the viscosity modifiers include polyacrylic acid, xanthan gum, sodium carboxymethylcellulose, carboxyvinyl polymers, polyoxyethylene glycol distearate, and ethanol. Examples of the stabilizers include ascorbic acid, sodium pyrosulfite, and EDTA. Examples of the pH adjusters include phosphate buffers and sodium hydroxide. Examples of the preservatives include ethyl parahydroxybenzoate, sodium benzoate, salicylic acid, sorbic acid, parabens (methylparaben, propylparaben, and the like), and sodium bisulfite.

The moisturizer, the cosmetic, and the external preparation for skin of the present invention can exhibit excellent effects on prevention, suppression, and treatment of chapped skin caused by aging, drying, skin diseases (atopic dermatitis and the like), and the like and also can exhibit an anti-wrinkle effect, an anti-stain effect, and an anti-freckle effect.

Other features of the invention will become apparent in the course of the following descriptions of exemplary embodiments which are given for illustration of the invention and are not intended to be limiting thereof.

EXAMPLES

Examples 1 to 5 and Comparative Examples 1 and 2. Comparison of Amplified Amount of Gene of Moisturizing-Related Portein by Octanoyl Neutral Amino Acids Human normal epidermal keratinocytes NHEK (NB) (manufactured by KURABO INDUSTRIES LTD.) were precultured with HuMedia-KG2 (manufactured by KURABO INDUSTRIES LTD.) and the precultured human normal epidermal keratinocytes were adjusted in a concentration of $30 \times 10^4$ cells/mL. After adjusting the concentration, 2 mL of the culture solution (that is, $60 \times 10^4$ cells/well) was poured to a plate having 6 wells and the poured culture solution was cultivated for 1 day. Samples (octanoyl-valine (Example 1: C8Val), octanoyl-alanine (Example 2: C8Ala) octanoyl-leucine (Example 3: C8Leu), octanoyl-isoleucine (Example 4: C8Ile), octanoyl-glycine (Example 5: C8Gly), glycylproline (Comparative Example 1: Gly-Pro), and valine (Comparative Example 2: Val)) were added to the wells so that each of the samples has the concentration illustrated in respective graphs and the added samples were reacted for 48 hours. After the reaction, entire RNA was extracted from the cells and subjected to reverse transcription. The amplified amounts of the target genes (filaggrin, involucrin, transglutaminase (TG) 1, keratin 10, and loricrin) were measured by real time PCR (n=2) and the measured amplified amounts were compared with the amplified amount of a control (no acyl neutral amino acid was added). GAPDH was used as a corrected gene. Calculation was carried out using a comparative CT method. TaqMan (registered trademark) Gene Expression was used as a primer and a probe and FAM was used as a fluorescent dye. The results are illustrated in FIGS. 1 and 2.

Figure 1:
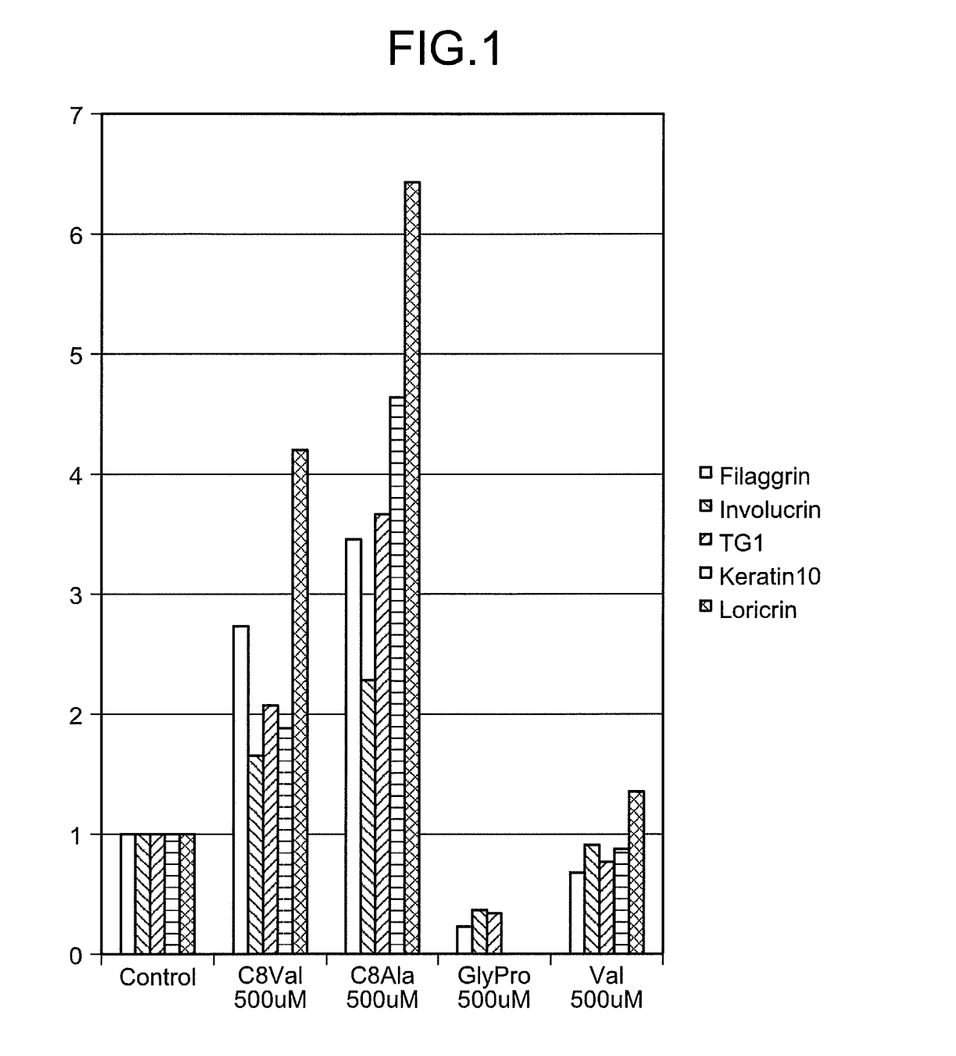
FIG. 1 is a graph illustrating the amplified amounts (relative values to the amplified amount of a control) of each moisturizing-related protein gene by octanoyl-valine (Example 1: C8Val), octanoyl-alanine (Example 2: C8Ala), glycylproline (Comparative Example 1: Gly-Pro), and valine (Comparative Example 2: Val).
Figure 2:
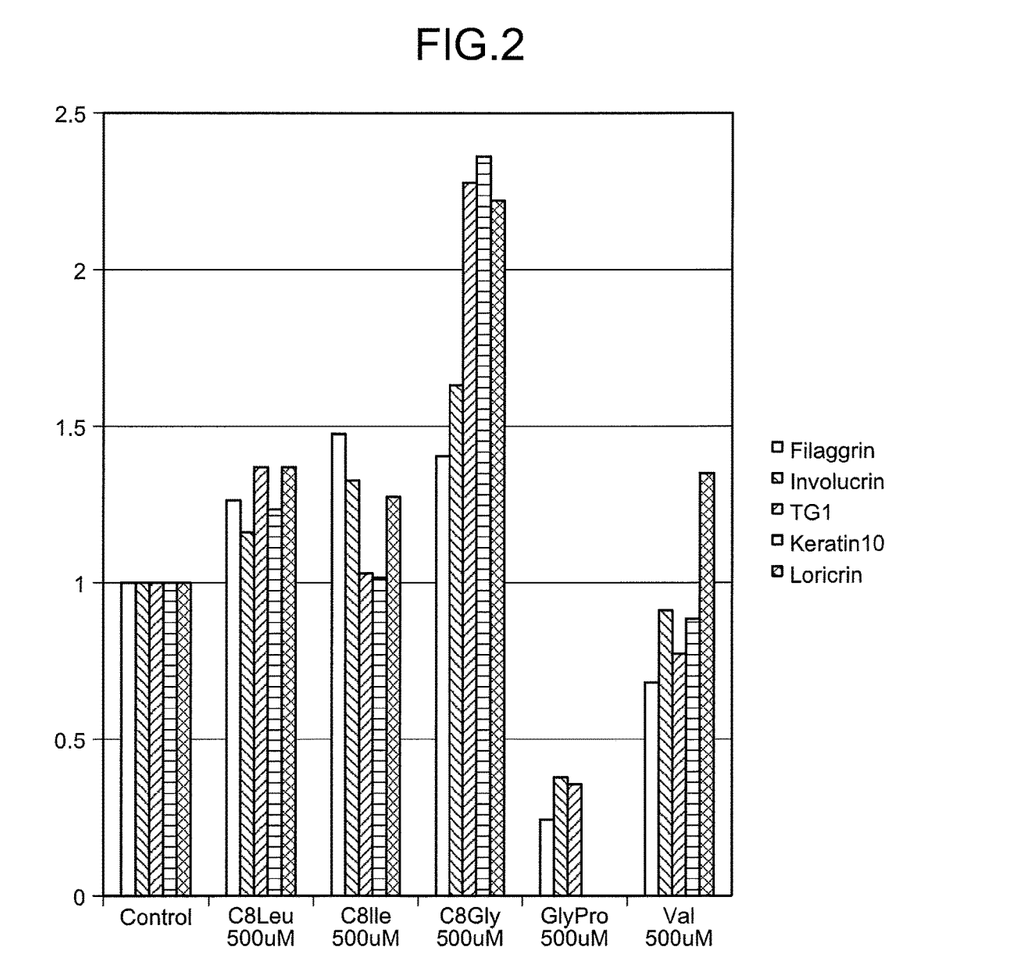
FIG. 2 is a graph illustrating the amplified amounts (relative values to the amplified amount of the control) of each moisturizing-related protein gene by octanoyl-leucine (Example 3: C8Leu), octanoyl-isoleucine (Example 4: C8Ile), octanoyl-glycine (Example 5: C8Gly), glycylproline (Comparative Example 1: Gly-Pro), and valine (Comparative Example 2: Val).

As is clear from FIGS. 1 and 2, the amplified amounts of each of the target genes in Examples 1 to 5 were larger than those of Comparative Examples 1 and 2. These results indicate that the acyl neutral amino acids can promote the production of the moisturizing-related proteins and can exhibit the moisturizing effect when the acyl neutral amino acids are included in cosmetics.

Examples 6 to 11. Comparison of Amplified Amount of Gene of Moisturizing-Related Protein by Acyl Valines The comparison was carried out in the same manner as Example 1 except that the samples (butanoyl-valine (Example 6: C4Val), hexanoyl-valine (Example 7: C6Val), octanoyl-valine (Example 8: C8Val), decanoyl-valine (Example 9: C10Val), dodecanoyl-valine (Example 10: C12Val), and acetyl-valine (Example 11: C2Val) were used and filaggrin, involucrin, and transglutaminase (TG) 1 were determined to be the target genes. The results are illustrated in FIG. 3.

Figure 3:
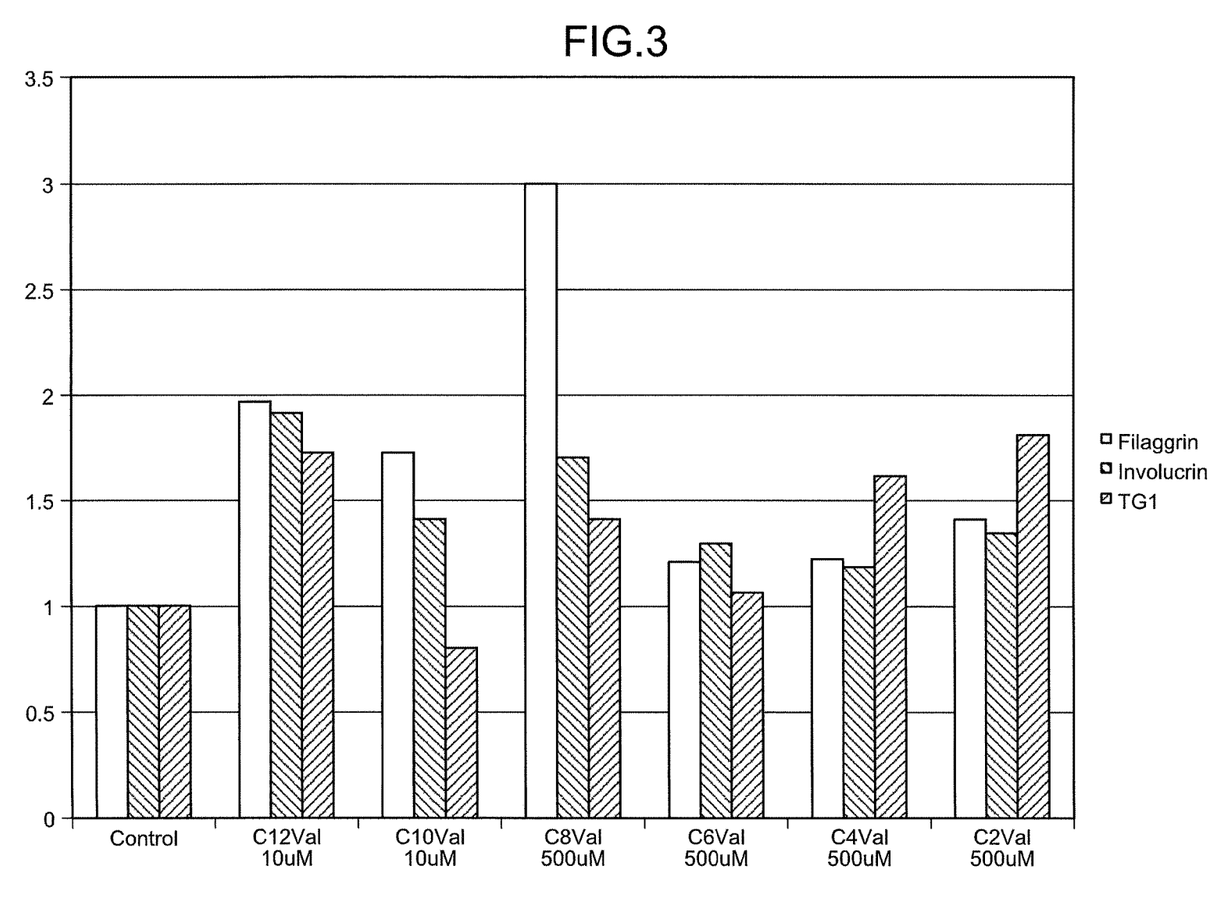
FIG. 3 is a graph illustrating the amplified amounts (relative values to the amplified amount of the control) of each moisturizing-related protein gene by butanoyl-valine (Example 6: C4Val), hexanoyl-valine (Example 7: C6Val), octanoyl-valine (Example 8: C8Val), decanoyl-valine (Example 9: C10Val), dodecanoyl-valine (Example 10: C12Val), and acetyl-valine (Example 11: C2Val).

As is clear from FIG. 3, the amplified amounts of each of the target genes in any of Examples 6 to 11 were larger than the amplified amounts of the control. These results indicate that the acyl neutral amino acids involving an acyl group having a carbon atom number of 2 to 12 and the salts thereof can promote the production of the moisturizing-related protein regardless of the kinds of the acyl groups and can exhibit the moisturizing effect when the acyl neutral amino acids are included in cosmetics, which indicates that the acyl neutral amino acids and the salts thereof are useful as the active components of the cosmetics.

Examples 12 and 13 and Comparative Examples 3 and 4

About 1 g of each compound was precisely weighed in a weighing bottle and the weighed samples were placed in a constant-temperature and constant-humidity chamber (LH-30-10, manufactured by NAGANO SCIENCE CO, LTD.) in which the humidity was set to 65% RH to measure a weight increase ratio (A) after 7 days. Subsequently, the same samples were placed in the constant-temperature and constant-humidity chamber in which the humidity was set to 35% RH to measure a weight increase ratio (B) after 7 days. It can be considered that, as the ratio of (B) to (A) becomes higher, more moisture can be retained even when the environment becomes low humidity and thus that the compound having the higher value of the ratio can be considered as a compound having higher moisturizing power. The studied results are listed in Table 1.

TABLE 1

Result of moisture absorption/retention test

| | Compound | Increased weight Ratio after 7 days at 65% RH (%) (A) | Increased weight ratio after 7 days at 35% RH (%) (B) | (B)/(A) × 100(%) |
|---|---|---|---|---|
| Example 12 | N-octanoyl-L-valine sodium salt | 25.4 | 8.4 | 33.2 |
| Example 13 | N-octanoyl-L-alanine sodium salt | 29.6 | 10.6 | 35.9 |
| Comparative Example 3 | Glycerol | 48.1 | 13.2 | 27.4 |
| Comparative Example 4 | Sorbitol | 4.2 | 0.5 | 12.0 |

As is clear from Table 1, a N-octanoyl-L-valine sodium salt in Example 12 and a N-octanoyl-L-alanine sodium salt in Example 13 exhibited high moisturizing power compared with glycerol in Comparative Example 3 and sorbitol in Comparative Example 4, which are generally believed as raw materials for cosmetic products having high moisturizing power. These results indicate that the acyl neutral amino acids involving an acyl group having a carbon atom number of 2 to 18 and the salts thereof are presumed to promote the production of the moisturizing-related proteins regardless of the kinds of the acyl groups and can exhibit the moisturizing effect, which indicates that the acyl neutral amino acids and the salts thereof are useful as active components of the cosmetics.

Figure 4:
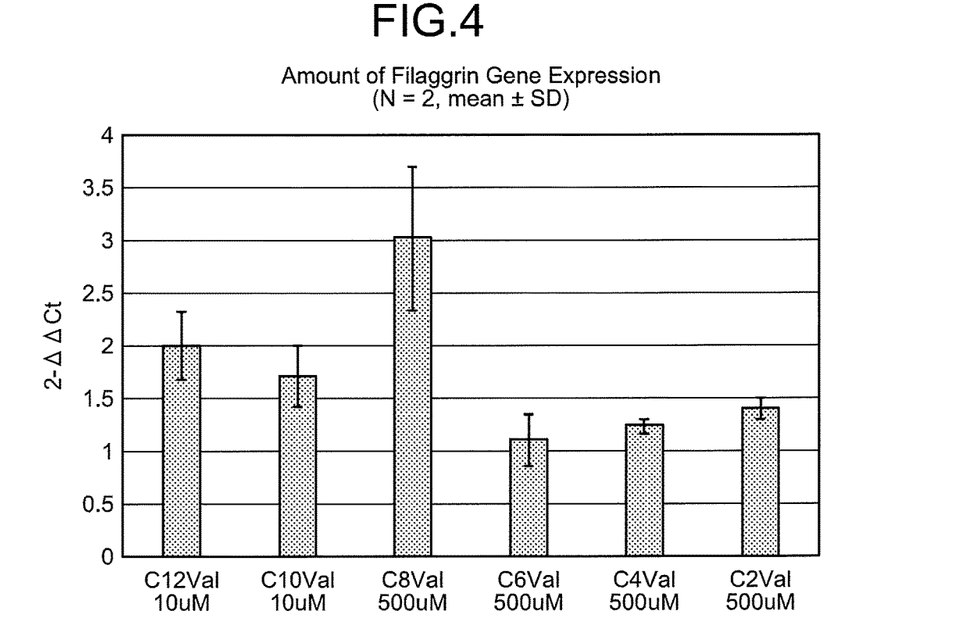
FIG. 4 is a graph illustrating the amplified amounts (relative values to the amplified amount of the control) of filaggrin gene by lauroyl-valine (Example 14: C12Val), decanoyl-valine (Example 15: C10Val), octanoyl-valine (Example 16: C8Val), hexanoyl-valine (Example 17: C6Val), butanoyl-valine (Example 18: C4Val), and acetyl-valine (Example 19: C2Val).
Figure 5:
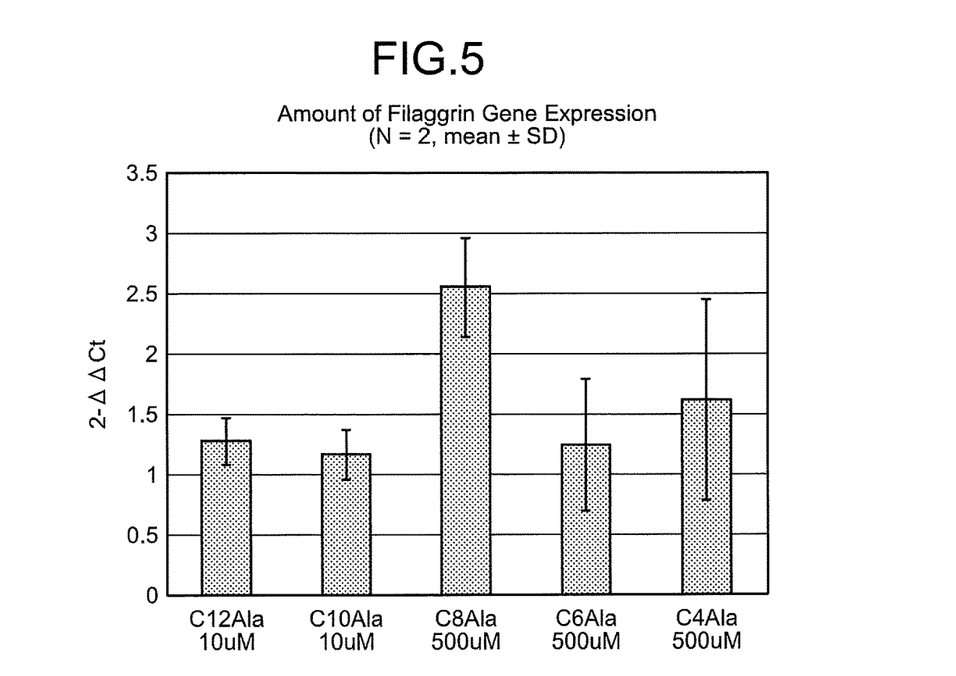
FIG. 5 is a graph illustrating the amplified amounts (relative values to the amplified amount of the control) of filaggrin gene by lauroyl-alanine (Example 20: C12Ala), decanoyl-alanine (Example 21: C10Ala), octanoyl-alanine (Example 22: C8Ala), hexanoyl-alanine (Example 23: C6Ala), and butanoyl-alanine (Example 24: C4Ala).

Examples 14 to 24. Comparison of Amplified Amount of Filaggrin Gene by Acyl Valines or Acyl Alanines Human normal epidermal keratinocytes NHEK (NB) (manufactured by KURABO INDUSTRIES LTD.) were precultured with HuMedia-KG2 (manufactured by KURABO INDUSTRIES LTD.) and the precultured human normal epidermal keratinocytes were adjusted in a concentration of $15 \times 10^4$ cells/mL. After adjusting the concentration, 2 mL of the culture solution (that is, $30 \times 10^4$ cells/well) was poured to a plate having 6 wells and the poured culture solution was cultivated for 1 day. Samples (lauroyl-valine (Example 14: C12Val), decanoyl-valine (Example 15: C10Val), octanoyl-valine (Example 16: C8Val), hexanoyl-valine (Example 17: C6Val), butanoyl-valine (Example 18: C4Val), and acetyl-valine (Example 19: C2Val), lauroyl-alanine (Example 20: C12Ala), decanoyl-alanine (Example 21: C10Ala), octanoyl-alanine (Example 22: C8Ala), hexanoyl-alanine (Example 23: C6Ala), and butanoyl-alanine (Example 24: C4Ala)) were added to the wells so that each of the samples has the concentration illustrated in respective graphs and the added samples were reacted for 24 hours. After the reaction, entire RNA was extracted from the cells and subjected to reverse transcription. The amplified amounts of the target gene (filaggrin) were measured by real time PCR (n=2). The amplified amount of the control (no acyl neutral amino acid was added) was determined to be 100% and the measured values were compared with this value. GAPDH was used as a corrected gene. Calculation was carried out using a comparative CT method. TaqMan (registered trademark) Gene Expression was used as a primer and a probe and FAM was used as a fluorescent dye.

The following evaluation was carried out depending on the amplified amounts. The results are listed in Table 2 and 3 and illustrated in FIGS. 4 and 5.
- A 200% or larger
- B 100% or larger and smaller than 200%
- C 50% or larger and smaller than 100%
- D Smaller than 50%

TABLE 2

Filaggrin gene expression test by acyl valines

| | Example 14 C12Val (10 μM) | Example 15 C10Val (10 μM) | Example 16 C8Val (500 μM) | Example 17 C6Val (500 μM) | Example 18 C4Val (500 μM) | Example 19 C2Val (500 μM) |
|---|---|---|---|---|---|---|
| Amplified amount (%) | 200 | 171 | 302 | 112 | 126 | 141 |
| Evaluation | A | B | A | B | B | B |

TABLE 3

Filaggrin gene expression test by acyl alanines

| | Example 20 C12Ala (10 μM) | Example 21 C10Ala (10 μM) | Example 22 C8Ala (500 μM) | Example 23 C6Ala (500 μM) | Example 24 C4Ala (500 μM) |
|---|---|---|---|---|---|
| Amplified amount (%) | 128 | 117 | 256 | 125 | 162 |
| Evaluation | B | B | A | B | B |

Examples 25 to 30. Comparison of Cytotoxicity of Acyl Valine

Figure 6:
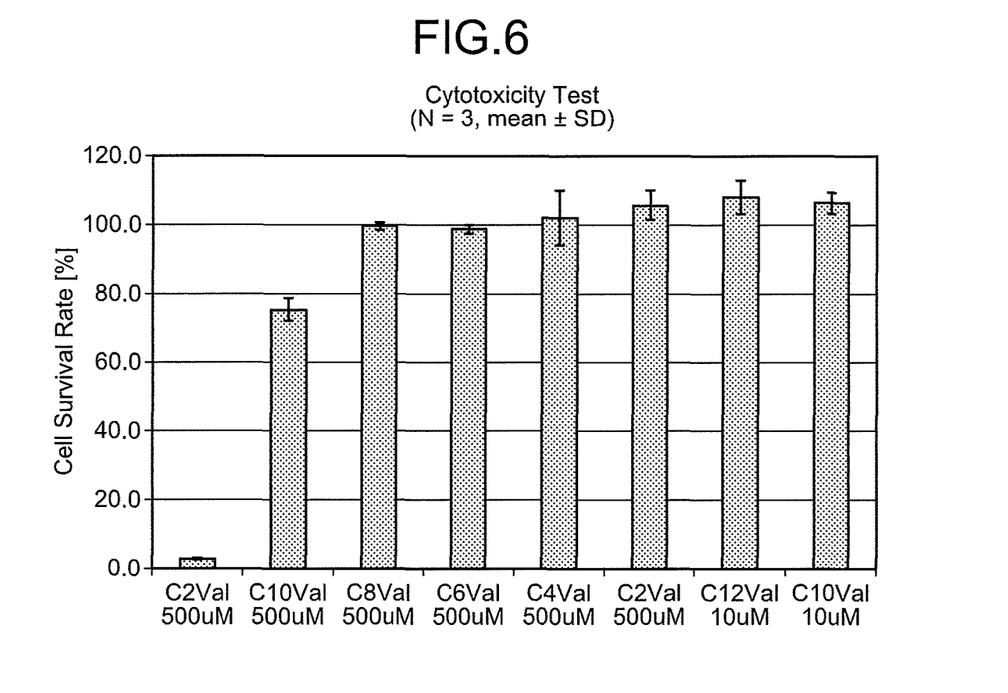
FIG. 6 is a graph illustrating cell survival rates (percentages relative to light absorbance of the control) by lauroyl-valine (Example 25: C12Val), decanoyl-valine (Example 26: C10Val), octanoyl-valine (Example 27: C8Val), hexanoyl-valine (Example 28: C6Val), butanoyl-valine (Example 29: C4Val), and acetyl-valine (Example 30: C2Val).

Human normal epidermal keratinocytes NHEK (NB) (manufactured by KURABO INDUSTRIES LTD.) were precultured with HuMedia-KG2 (manufactured by KURABO INDUSTRIES LTD.) and the precultured human normal epidermal keratinocytes were adjusted in a concentration of $15 \times 10^4$ cells/mL. After adjusting the concentration, 2 mL of the culture solution (that is, $30 \times 10^4$ cells/well) was poured to a plate having 6 wells and the poured culture solution was cultivated for 1 day. Samples (lauroyl-valine (Example 25: C12Val), decanoyl-valine (Example 26: C10Val), octanoyl-valine (Example 27: C8Val), hexanoyl-valine (Example 28: C6Val), butanoyl-valine (Example 29: C4Val), and acetyl-valine (Example 30: C2Val)) were added to the wells so that each of the samples has the concentration illustrated in respective graphs and the added samples were reacted for 24 hours. Thereafter, the culture medium was discarded and replaced with 2 mL/well of Neutral Red solution. The resultant sample was further cultured for 2 hours. As the Neutral Red solution, a solution prepared by diluting Neutral Red (manufactured by KURABO INDUSTRIES LTD.) with HuMedia-KG2 culture medium/normal saline solution (2:1) to 1/100 was used. The cells stained with the Neutral Red solution were washed with PBS (-) one time, thereafter fixed by 1.5 mL/well of 1% $CaCl_2$/1% formalin solution, extracted by adding 1.5 mL/well of 1% acetic acid/50% ethanol solution at room temperature for 20 minutes. The light absorbance of the resultant sample was measured using a plate reader at 540/630 nm.

The following evaluation was carried out depending on the cell survival rates. The results are listed in Table 4 and illustrated in FIG. 6.
- A 99% or higher
- B 75% or higher and lower than 99%
- C 50% or higher and lower than 75%
- D Lower than 50%

TABLE 4

Cytotoxicity test

| | Example 25 C12Val (500 μM) | Example 26 C10Val (500 μM) | Example 27 C8Val (500 μM) | Example 28 C6Val (500 μM) | Example 29 C4Val (500 μM) | Example 30 C2Val (500 μM) |
|---|---|---|---|---|---|---|
| Cell survival rate (%) | 3 | 75 | 100 | 99 | 102 | 105 |
| Evaluation | D | B | A | A | A | A |

Evaluation of Examples 14 to 24 indicates that each of the acyl neutral amino acids can amplify the filaggrin gene. Evaluation of Examples 25 to 30 indicates that the cytotoxicity of the acyl neutral amino acid in Example 25 is high, whereas the cytotoxicity of each of the acyl neutral amino acids in Examples 26 to 30 is low. When the evaluations of the amplified amount of the filaggrin gene and the cytotoxicity are summarized, it is clear that the acyl neutral amino acids involving an acyl group having a carbon atom number of 2 to 12 are preferable, the acyl neutral amino acids involving an acyl group having a carbon atom number of 2 to 10 are more preferable, and the acyl neutral amino acids involving an acyl group having a carbon atom number of 8 are further preferable.

Formulation Example 1 Skin Cream

A skin cream was prepared by preparing and mixing A, B, and C in the compositions listed in Table 5.

TABLE 5

| | | (wt %) |
|---|---|---|
| A | Liquid paraffin | 8.0 |
| | Isopropyl palmitate | 2.0 |
| | Stearyl alcohol | 2.0 |
| | Cetyl alcohol | 0.5 |
| | Glyceryl monostearate | 0.5 |
| | POE (20) cetyl ether | 1.0 |
| | Propyl paraoxybenzoate | 0.1 |
| B | "PRODEW" 400 | 4.4 |
| | Carboxyvinyl polymer(0.5%) | 20.0 |
| | Octanoyl-valine | 1.0 |
| | Purified water | Balance |
| | Methyl paraoxybenzoate | 0.1 |
| C | Sodium hydroxide (1%) | 4.0 |
| | | 100.0 |

Formulation Example 2 Emulsion

An emulsion was prepared by preparing and mixing A, B, C, D, and E in the compositions listed in Table 6.

TABLE 6

| | | (wt %) |
|---|---|---|
| A | PEG-10 hydrogenated castor oil | 0.25 |
| | PEG-20 hydrogenated castor oil | 2.25 |
| | "ELDEW" PS-203 | 1.00 |
| | Mineral oil | 9.00 |
| | Glycerol | 10.00 |
| B | (Acrylates/alkyl acrylate(C10-30)) cross-polymer*4 | 0.50 |
| | Water | 49.50 |
| C | Hydroxyethyl cellulose | 0.07 |
| | Water | 6.93 |
| D | L-arginine | 0.40 |
| | Octanoyl-alanine | 1.0 |
| | Water | 3.60 |
| E | AJIDEW NL-50 | 1.00 |
| | "PRODEW" 400 | 1.00 |
| | BG | 12.00 |
| | Water | Balance |
| | Preservative | Proper amount |
| | | 100.0 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A moisturizer, comprising at least one acyl neutral amino acid having an acyl group having a carbon atom number of 2 to 10 or a carbon number of 12 or a salt thereof.

2. The moisturizer according to claim 1, wherein said acyl neutral amino acid is an acyl leucine, an acyl isoleucine, an acyl valine, an acyl glycine, or an acyl alanine.

3. The moisturizer according to claim 1, wherein the carbon atom number of the acyl group is 12.

4. The moisturizer according to claim 1, wherein the carbon atom number of the acyl group is 2 to 10.

5. The moisturizer according to claim 1, wherein the carbon atom number of the acyl group is 8.

6. The moisturizer according to claim 1, wherein the acyl neutral amino acid is one or more compounds selected from the group consisting of an acyl valine, an acyl glycine, and an acyl alanine.

7. The moisturizer according to claim 1, wherein the moisturizer promotes production of one or more moisturizing-related proteins selected from the group consisting of filaggrin, involucrin, transglutaminase 1, keratin 10, and loricrin.

8. The moisturizer according to claim 1, wherein the moisturizer reduces growth of an inflammatory cytokine.

9. A cosmetic, comprising a moisturizer according to claim 1.

10. An external preparation for skin, comprising a moisturizer according to claim 1.

11. A method for moisturizing skin, comprising applying to skin of a subject in need thereof an effective amount of at least one acyl neutral amino acid having an acyl group having a carbon atom number of 2 to 10 or a carbon number of 12 or a salt thereof.

12. The method according to claim 11, wherein said acyl neutral amino acid is an acyl leucine, an acyl isoleucine, an acyl valine, an acyl glycine, or an acyl alanine.

13. The method according to claim 11, wherein the carbon atom number of the acyl group is 12.

14. The method according to claim 11, wherein the carbon atom number of the acyl group is 2 to 10.

15. The method according to claim 11, wherein the carbon atom number of the acyl group is 8.

16. The method according to claim 11, wherein the acyl neutral amino acid is one or more compounds selected from the group consisting of an acyl valine, an acyl glycine, and an acyl alanine.

17. A method for promoting production of one or more moisturizing-related proteins selected from the group consisting of filaggrin, involucrin, transglutaminase 1, keratin 10, and loricrin, comprising applying to skin of a subject in need thereof an effective amount of at least one acyl neutral amino acid having an acyl group having a carbon atom number of 2 to 10 or a carbon number of 12 or a salt thereof.

18. The method according to claim 17, wherein said acyl neutral amino acid is an acyl leucine, an acyl isoleucine, an acyl valine, an acyl glycine, or an acyl alanine.

19. The method according to claim 17, wherein the carbon atom number of the acyl group is 12.

20. The method according to claim 17, wherein the carbon atom number of the acyl group is 2 to 10.

21. The method according to claim 17, wherein the carbon atom number of the acyl group is 8.

22. The method according to claim 17, wherein the acyl neutral amino acid is one or more compounds selected from the group consisting of an acyl valine, an acyl glycine, and an acyl alanine.

23. A method for reducing growth of an inflammatory cytokine, comprising applying to skin of a subject in need thereof an effective amount of at least one acyl neutral amino acid involving having an acyl group having a carbon atom number of 2 to 10 or a carbon number of 12 or a salt thereof.

24. The method according to claim 23, wherein said acyl neutral amino acid is an acyl leucine, an acyl isoleucine, an acyl valine, an acyl glycine, or an acyl alanine.

25. The method according to claim 23, wherein the carbon atom number of the acyl group is 12.

26. The method according to claim 23, wherein the carbon atom number of the acyl group is 2 to 10.

27. The method according to claim 23, wherein the carbon atom number of the acyl group is 8.

28. The method according to claim 23, wherein the acyl neutral amino acid is one or more compounds selected from the group consisting of an acyl valine, an acyl glycine, and an acyl alanine.

* * * * *